United States Patent
Maltese

(10) Patent No.: US 6,652,519 B2
(45) Date of Patent: Nov. 25, 2003

(54) ELECTRODE NEEDLE WITH RADIOFREQUENCY ACTIVE FILAMENT

(75) Inventor: Michele Maltese, Rodengo Saiano (IT)

(73) Assignee: Thermo-Med 2000 KFT (HU)

( * ) Notice: Subject to any disclaimer, the term of this patent is extended or adjusted under 35 U.S.C. 154(b) by 0 days.

(21) Appl. No.: 10/010,686

(22) Filed: Nov. 8, 2001

(65) Prior Publication Data

US 2002/0058937 A1 May 16, 2002

(30) Foreign Application Priority Data

Nov. 10, 2000 (IT) .................................... BS2000A0115

(51) Int. Cl.[7] .............................................. A61B 18/18
(52) U.S. Cl. ........................................ 606/41; 607/101
(58) Field of Search ..................... 606/41, 42, 45–50; 607/101, 102; 600/374

(56) References Cited

U.S. PATENT DOCUMENTS

| | | | | |
|---|---|---|---|---|
| 5,472,441 A | * | 12/1995 | Edwards et al. | 606/41 |
| 5,507,743 A | * | 4/1996 | Edwards et al. | 606/41 |
| 5,611,799 A | * | 3/1997 | Smith | 606/32 |
| 6,228,109 B1 | * | 5/2001 | Tu et al. | 607/113 |
| 6,231,573 B1 | * | 5/2001 | Amor et al. | 606/49 |
| 6,258,086 B1 | * | 7/2001 | Ashley et al. | 606/41 |
| 6,280,441 B1 | * | 8/2001 | Ryan | 606/45 |

* cited by examiner

*Primary Examiner*—Michael Peffley
(74) *Attorney, Agent, or Firm*—McGlew and Tuttle, P.C.

(57) ABSTRACT

Electrode needle for the treatment of parenchymatous tumours through radiofrequency-induced interstitial hyperthermy, comprising a hollow guide needle (11) and a radiofrequnecy active filament (12) threaded into the needle, connectable to a radiofrequency generator and capable of axial movements between an inactive position retracted into the needle and an active position of protrusion of a terminal segment of the filament from the distal end of the needle, characterised in that said terminal segment (13) of the filament is shaped to pass from a rectilinear shape when the filament is in retracted into the needle, to a spiral shape when the filament is in the active forward position.

15 Claims, 3 Drawing Sheets

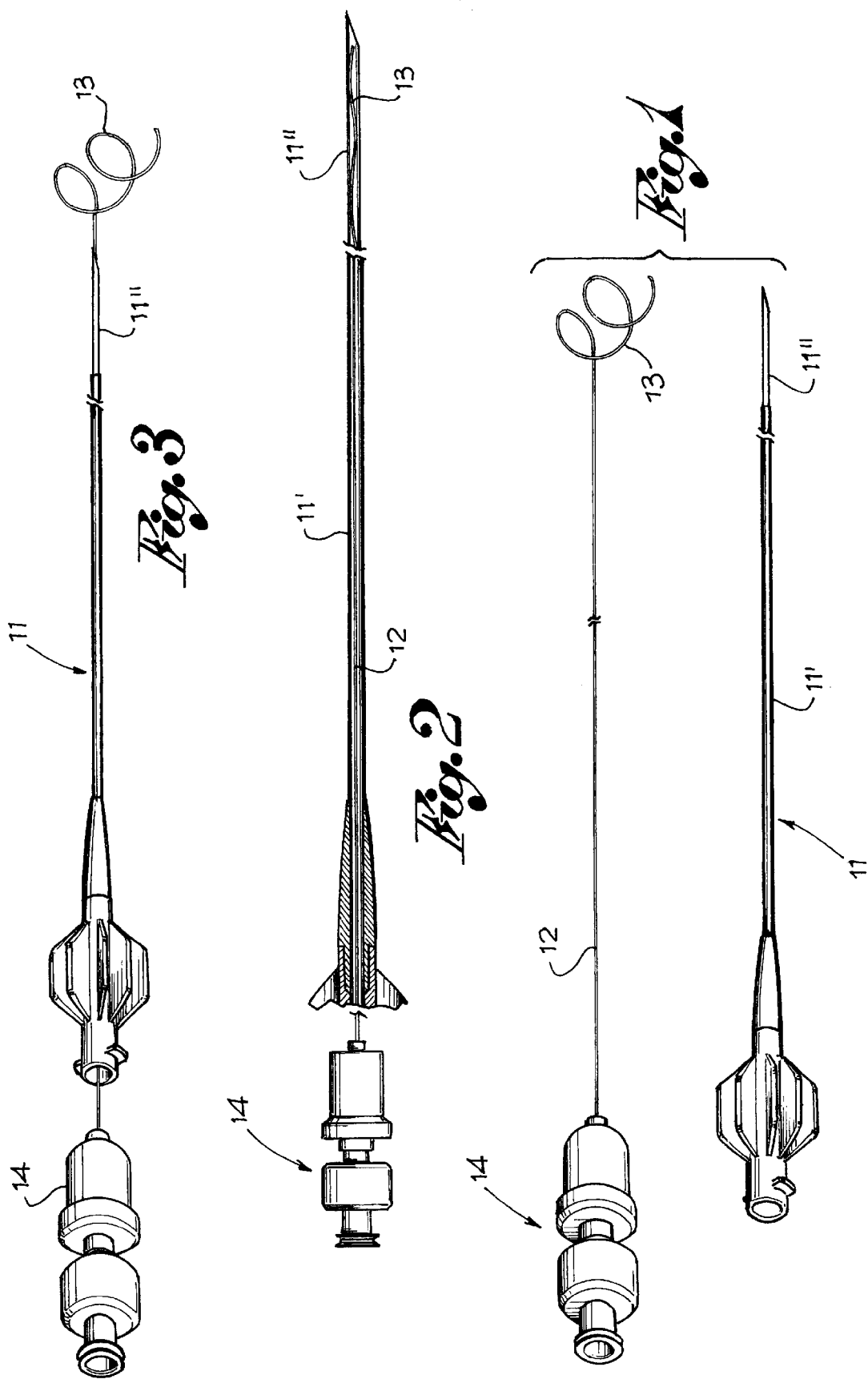

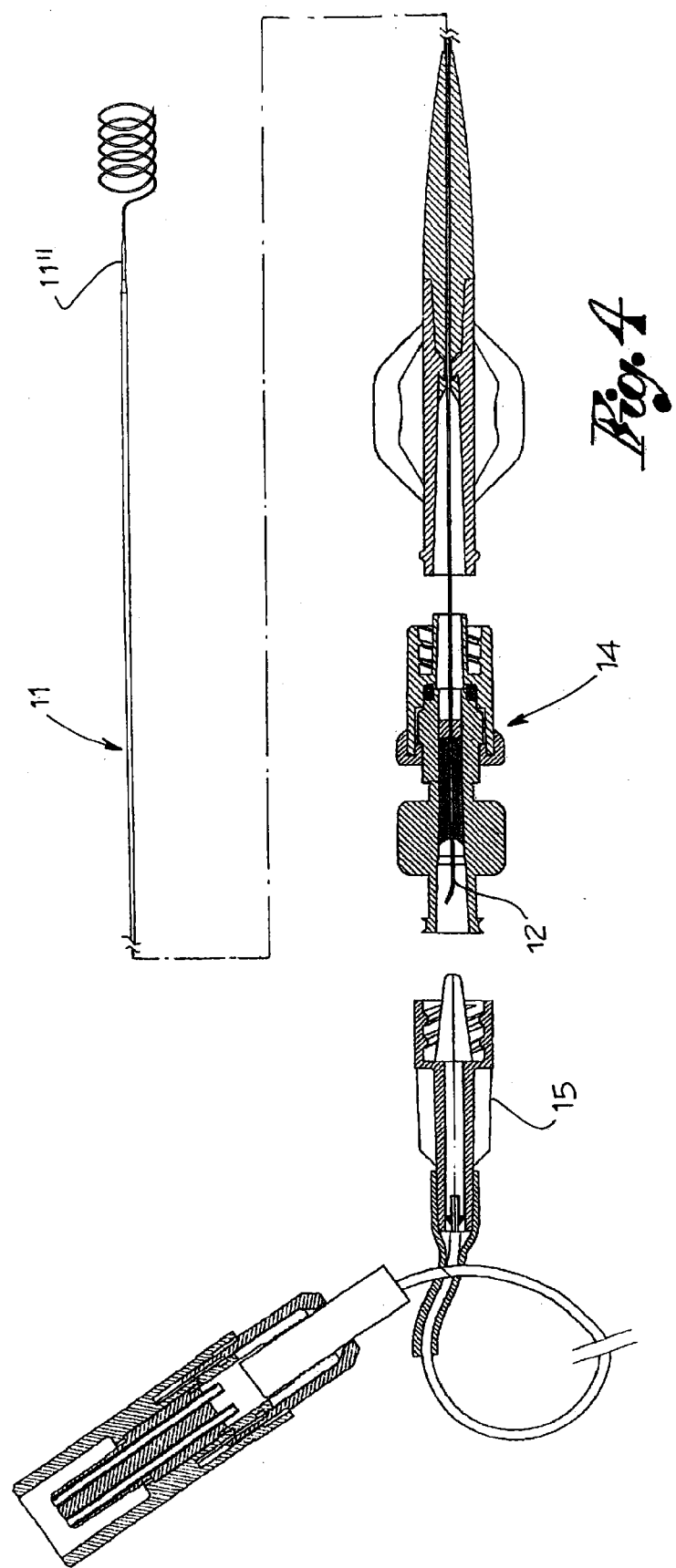

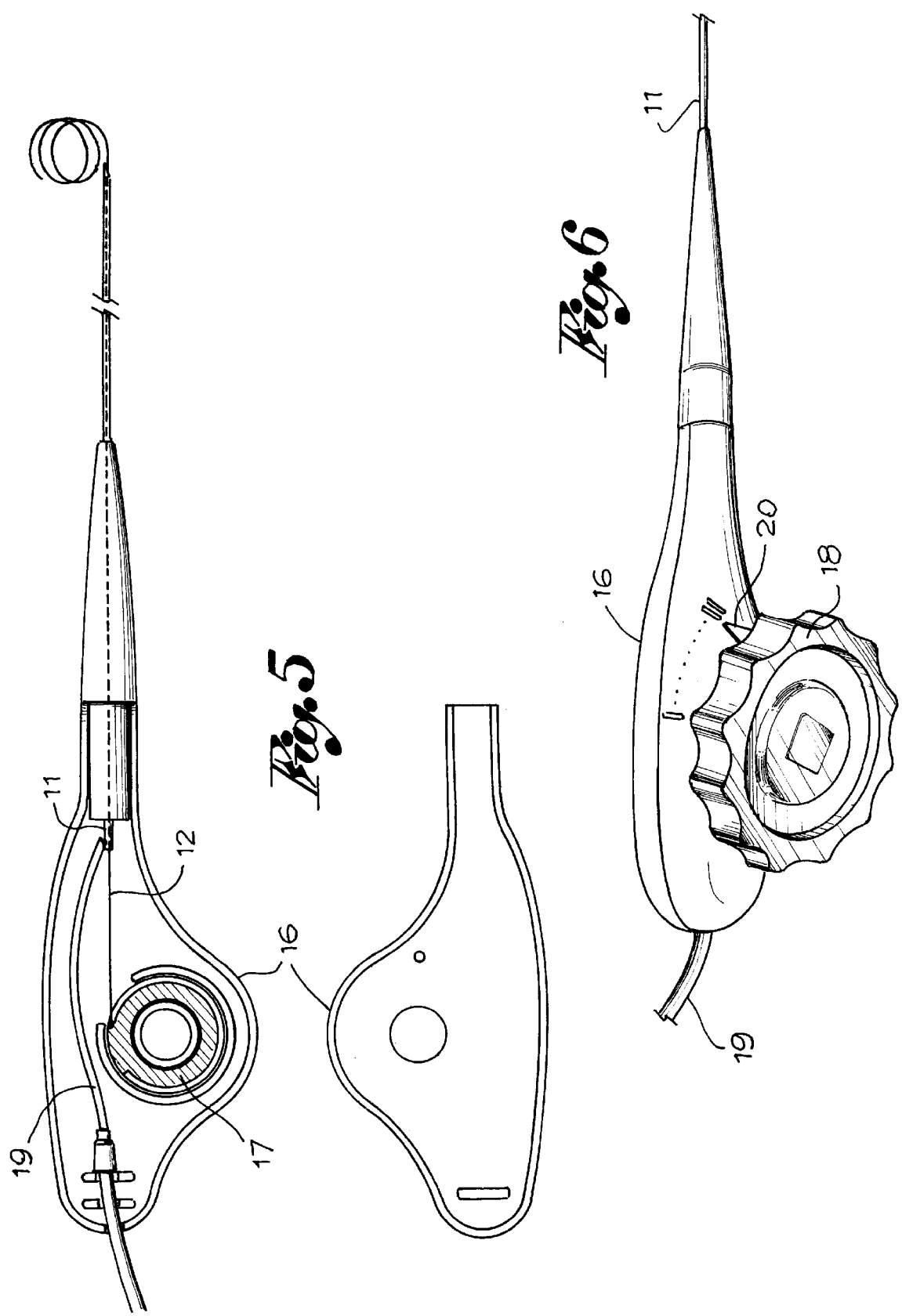

ELECTRODE NEEDLE WITH RADIOFREQUENCY ACTIVE FILAMENT

FIELD OF THE INVENTION

The present invention relates to an electrode needle, in particular for the treatment of parenchymatous tumours through radiofrequency-induced hyperthermy.

BACKGROUND OF THE INVENTION

The treatment of tumoral masses through radiofrequency-induced hyperthermy has already been proposed with success. The instruments currently available for such treatment are catheter tubes with at least one terminal electrode, or needles with a rectilinear radiofrequency active filament.

However, catheter tubes are relatively large and, even though they are efficient due to the presence of a big electrode, they exhibit the disadvantage that they can only be introduced into the patient's body up to the tumoral mass through natural open ways or ways opened through expansion.

On the other hand, needles with an active filament can be introduced into the body making them pass through the tissues, but they are limited in their action due to the small diameter of the active filament, which operates, on limited areas and thus implies longer operation and treatment times. On the other hand, if larger needles are use for the treatment of larger tumoral masses, the use of such needles is more traumatic for the patient.

SUMMARY OF THE INVENTION

The purpose of the finding is that of finding a remedy for the limitations of known instruments, thus providing a radiofrequency active electrode needle that could be used in the treatment of even considerable tumoral masses, maintaining in any case its limited diameter to reduce the traumatic effect and allow reaching organs or parts of organs that could not be otherwise reached with larger needles or tubes.

The purpose and resulting advantages are achieved with an instrument comprising a hollow guide needle and a radiofrequency active filament threaded, and sliding into, said needle between a retracted position, withdrawn into the needle, and a forward position emerging from the distal end of the needle and where said filament has a terminal segment bending in a helical or spiral shape when the filament is in the forward position.

Thanks to such helical and/or spiral arrangement of a terminal part, even though the active filament is very thin, it is capable of irradiating and thus treating a much larger surrounding area than the area of its section.

In other words, starting from a very thin guide needle and radiofrequency active filament, it is possible to easily treat tumoral masses that are at least as wide as the width of the helical or spiral part of the filament.

Further details of the finding will appear more clearly from the following description, made with reference to the attached indicative and nonlimiting drawings. In such drawings:

BRIEF DESCRIPTION OF THE DRAWINGS

FIG. 1 shows separate needle and active filament according to a first embodiment;

FIG. 2 shows a longitudinal section of the needle of FIG. 1 with the filament threaded in a retracted position;

FIG. 3 shows the needle with the filament in forward position for use;

FIG. 4 shows a longitudinal section of the electrical connection means to use the electrode needle of the previous Figures;

FIG. 5 shows a needle with a threaded filament in a second embodiment and with open connector; and FIG. 6 shows a perspective view of a detail of the handling means of the filament threaded in the needle of the previous Figure.

DESCRIPTION OF A PREFERRED EMBODIMENT

In such drawings, reference numeral 11 indicates a guide needle intended to be introduced into the body of a patient, and reference numeral 12 indicates a radiofrequency active filament, sized to be threaded, and to slide, into needle 11. The filament is rectilinear except for a distal terminal part 13 shaped as a helix or a spiral, for example through a thermoforming process. Such terminal part 13 can be in axis with respect to the main longitudinal direction of the needle, or angular, for example up to 90°.

For the constructional purposes, the needle has an external insulating coating 11' for its entire length, except for a part at the distal end 11".

According to a first embodiment shown in FIGS. 1–4, the proximal end of the radiofrequency filament 12 protrudes from the needle and is buried into a union 14, for example through a resin casting, which in any case is exposed for the contact with a filament electrical connection connector 15 to a radiofrequency generator, not shown.

Once it has been threaded into the guide needle, or keeping it still, the filament can be made to slide forward and backward through union 14, between an inactive position in which it is completely retracted into the needle, and an active position in which the terminal part 13 protrudes from the distal end of the needle.

In a second embodiment shown in FIGS. 5 and 6, the proximal end of the guide needle 11 is introduced into a connector 16 wherein there is housed a small shaft 17 capable of rotating around a perpendicular axis with respect to the needle through a hand grip 18.

The proximal end of the active filament 12 is engaged with said shaft 17 so that, when the hand grip 18 is rotated in clockwise or counter clockwise direction, the terminal part 13 of the filament respectively protrudes from or withdraws into, the needle. In this case, the electrical power supply cable 19 is directly inserted into connector 16 and is connected to the distal end of the guide needle 11.

To have an indication of the position of the active filament 12 with respect to the guide needle 11, once it has been introduced into the patient's body, the hand grip 18 can be associated to a pointer 20 angularly movable between at least two reference points provided on the connector. For its angular movements, said pointer can exhibit, for example, a pin interacting with a spiral Structure obtained on the inner side of the hand grip 18.

Irrespective of the embodiment, moreover, a thermocouple—not shown—can be applied on the distal part of the guide needle 11 for measuring the body temperature.

In practice, when the needle is introduced into the patient's body, the filament is held in an inactive retracted position, and its terminal part 13 remains substantially rectilinear, contained in the needle recess, as shown in FIG. 2. When the tumoral mass to be irradiated has been reached, the terminal part 13 is pushed from the needle, and winds up as a spiral or helix, as shown in FIGS. 3 and 4, thus affecting a wide irradiation area.

Once the treatment has finished, the terminal part of the filament is withdrawn into the needle.

It must be noted that the effectiveness of the electrode needle can be further improved using more active filaments threaded into the same guide needle and configured as described above.

Finally, it must be noted that the electrode needle being examined can also be used in combination with other electromagnetic wave generators, for example microwave generators.

What is claimed is:

1. An electrode needle for the treatment of parenchymatous tumours through radiofrequency-induced interstitial hyperthermy, the electrode needle comprising:
   a hollow guide needle; and
   at least a radiofrequency active filament threaded into the needle, said radiofrequency active filament being connectable to a radiofrequency generator and being capable of axial movements between an inactive position retracted into the needle and an active position in which a terminal segment of the filament of protrudes from a distal end of the hollow guide needle, said terminal segment having a shape changing from a rectilinear shape when the filament is in said inactive position, to a helical shape a when the filament is in said active position, said terminal helical shape having an axis being angled with respect to the longitudinal direction of the needle.

2. An electrode needle according to claim 1, wherein said terminal helical shape is 90° angled with respect to the longitudinal direction of the needle.

3. An electrode needle according to claim 1, wherein said terminal helical shape is spiral.

4. An electrode needle according to claim 1, wherein the needle is provide with an external insulating coating and a noninsulated distal part.

5. An electrode needle according to claim 1, further comprising a thermocouple applied on a distal part of said guide needle.

6. A method of using a filament having a terminal segment preformed into a hollow guide needle for the treatment of tumours through radiofrequency induced hyperthermy, the method comprising the steps of:
   providing an electrode needle with a hollow guide needle and a radiofrequency active filament threaded into the needle, said radiofrequency active filament being connectable to a radiofrequency generator and being capable of axial movements between an inactive position retracted into the needle and an active position in which a terminal segment of the filament protrudes from a distal end of the hollow guide needle;
   providing said terminal segment in a rectilinear shape when in said inactive position retracted into the needle; and
   providing said terminal segment in a spiral or helical shape when in said active position emerging from said needle.

7. A method according to claim 6 wherein said spiral or helical shape filament terminal segment is oriented with a helix axis substantially at 90° to an axis of said needle.

8. A method according to claim 6 further comprising providing a thermocouple located on a distal section of said needle for measuring body temperature.

9. An electrode needle for providing radiofrequency-induced intersticial hyperthermia treatment, the electrode needle comprising:
   a hollow guide needle, said needle having an insulating coating on its entire length except for a tip portion at a tip of said needle and for a proximal end section at a base end of said needle, said proximal end section of said needle being connected to a power supply cable; and
   at least one radiofrequency active filament threaded through said guide needle, said filament having a proximal end engaged with a shaft located in a housing enclosing said base of said needle, and a distal end with a terminal section having an elastically deformable preset helical form, wherein said filament may be moved, by rotation of said shaft, between a retracted position within said needle where said terminal end of said filament does not protrude beyond the tip of said needle with said filament terminal section being confined in a rectilinear state by said needle, and an extended position wherein said filament terminal end protrudes from the tip of said needle and elastically takes said helical shape, with an axis of said helix of said filament terminal section forming an angle of up to 90° with an axis of said needle.

10. An electrode needle according to claim 9, further comprising:
    a hand grip connected to said shaft for rotating said shaft.

11. An electrode needle according to claim 10, further comprising:
    reference markings on said housing, and a pointer connected to said hand grip and correlating to said reference markings, for indicating an extension of said filament relative to a rotational position of said hand grip.

12. An electrode needle according to claim 9, wherein said angle between said helix axis and said needle axis is between 45° and 90°.

13. An electrode needle according to claim 9, wherein said angle between said helix axis and said needle axis is 90°.

14. An electrode needle according to claim 9, wherein said helical form of said filament terminal section has a spiral component.

15. An electrode needle according to claim 9, further comprising a thermocouple applied to a distal part of said guide needle.

* * * * *